(12) United States Patent
Bakker-Arkema et al.

(10) Patent No.: US 7,192,951 B2
(45) Date of Patent: Mar. 20, 2007

(54) TREATMENT OF CONGESTIVE HEART FAILURE

(75) Inventors: Rebecca Guggemos Bakker-Arkema, Ann Arbor, MI (US); Milton Lethan Pressler, Saline, MI (US)

(73) Assignee: Astellas Pharma Inc. (JP)

(*) Notice: Subject to any disclaimer, the term of this patent is extended or adjusted under 35 U.S.C. 154(b) by 0 days.

(21) Appl. No.: 11/154,909

(22) Filed: Jun. 16, 2005

(65) Prior Publication Data
US 2005/0245506 A1 Nov. 3, 2005

Related U.S. Application Data

(63) Continuation of application No. 10/799,415, filed on Mar. 12, 2004, now abandoned, which is a continuation of application No. 10/129,892, filed as application No. PCT/US01/09265 on Mar. 22, 2001, now abandoned.

(60) Provisional application No. 60/201,431, filed on May 3, 2000.

(51) Int. Cl.
*A61K 31/55* (2006.01)
*A61K 31/34* (2006.01)
(52) U.S. Cl. ............................ 514/215; 514/471
(58) Field of Classification Search ..................... None
See application file for complete search history.

(56) References Cited

U.S. PATENT DOCUMENTS

| 5,225,402 | A | 7/1993 | Ogawa et al. |
| 5,256,687 | A | 10/1993 | Becker et al. |
| 5,258,510 | A | 11/1993 | Hidenori et al. |
| 5,338,755 | A | 8/1994 | Wagnon et al. |
| 5,719,155 | A | 2/1998 | Cho et al. |
| 5,723,606 | A * | 3/1998 | Tanaka et al. ............... 540/578 |
| 6,420,358 | B1 * | 7/2002 | Ellis-Grosse et al. ....... 514/220 |

FOREIGN PATENT DOCUMENTS

| EP | 0205334 | 12/1986 |
| EP | 0344995 | 12/1989 |
| EP | 0365134 | 4/1990 |
| EP | 0229329 | 7/1993 |
| WO | WO 98/25901 | 6/1998 |

OTHER PUBLICATIONS

PCT International Search Report, PCT/US01/09265, date not available.

Chan, et al, "VPA-985, a nonpeptide orally active and selective vasopressin V2 receptor antagonist", Advances in Experimental Medicine and Biology, vol. 449, 1998 pp. 439-443.
Swan, et al, "Interaction between VPA-985, and ADH (V2) antagonist and furosemide", Journal of the American Society of Nephrology, vol. 10, 1999, pp. 124A.
Taneja, et al, "Current status of acute intravenous therapy for chronic heart failure exacerbations", Congestive Heart Failure, vol. 5, No. 5, 1999, pp. 199-207, 215.
Hirano, et al., "Effects of the V2-Receptor Antagonist OPC-41061 and the Loop Diuretic Forosemide Alone and in Combination in Rats", The Journal of Pharmacology and Experimental Therapeutics, 2000, pp. 288-294, vol. 292(1).
Tammara, et al, Pharmacokinetic and Pharmacodynamic Interaction Between OPC-41061 Furosemide and Hydrochlorothiazide, date/source unavailable.

* cited by examiner

*Primary Examiner*—Raymond J. Henley, II
(74) *Attorney, Agent, or Firm*—Finnegan, Henderson, Farabow, Garrett & Dunner, LLP

(57) ABSTRACT

Combinations of diuretics and vasopressin antagonists are useful to slow and reverse the symptoms and process of congestive heart failure, to increase the excretion of water in the urine, and to decrease the excretion of sodium and potassium ions in urine. Preferred vasopressin antagonists have the formula

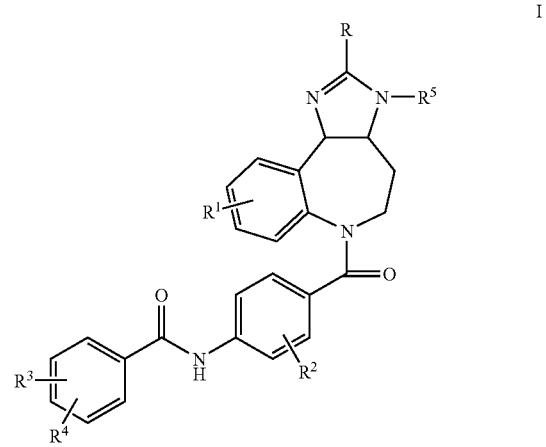

wherein R and $R^5$ are hydrogen or lower alkyl;
$R^1$, $R^2$, and $R^3$ are hydrogen, halo, alkyl, alkoxy, and amino; and
$R^4$ is hydrogen or phenyl, and a pharmaceutically acceptable salt thereof.

4 Claims, 4 Drawing Sheets

TREATMENT OF CONGESTIVE HEART FAILURE

This is a continuation of U.S. patent application Ser. No. 10/799,415, filed Mar. 12, 2004, now abandoned, which is a continuation of U.S. patent application Ser. No. 10/129,892, filed May 9, 2002, now abandoned, which is the National Stage of International Application PCT/US01/09265, filed Mar. 22, 2001, which was published in English, which claims priority to U.S. Provisional Application Ser. No. 60/201,431, filed May 3, 2000.

FIELD OF THE INVENTION

This invention relates to combinations of vasopressin antagonists and diuretic agents for use in treating edematous conditions such as congestive heart failure.

BACKGROUND OF THE INVENTION

Congestive heart failure (CHF) is a pathophysiological state in which the heart is unable to pump sufficient blood to meet the metabolic needs of the body. The underlying basis of this disorder is a deficiency of myocardial contractility, resulting in a decreased mechanical ability to pump blood and in turn, a decreased cardiac output. Congestive heart failure may result from a number of factors affecting the myocardium, altering systolic and/or diastolic function. As the condition progresses, activation of both the sympathetic nervous system and the renin-angiotensin-aldosterone system lead to an increase in the total peripheral resistance. In addition, elevated levels of arginine vasopressin (AVP) have been reported in some patients with heart failure, although its pathophysiologic role is unknown. It has been postulated that the increase in AVP may provide increased systemic vascular resistance and impaired water excretion as a compensatory mechanism to the low cardiac output associated with CHF.

Arginine vasopressin, also known as antidiuretic hormone (ADH), is synthesized in the magnocellular neurosecretory cells of the paraventricular and supraoptic nuclei of the hypothalamus and stored in the posterior pituitary. There are 2 classes of AVP receptors, $V_1$ and $V_2$. There are 2 subclasses of $V_1$ receptors, $V_{1A}$ and $V_{1B}$. $V_{1A}$ receptors are found in the vasculature, and mediate the pressor response of AVP by increasing the contraction of blood vessels. $V_{1A}$ receptors are also found on platelets, where they mediate platelet aggregation. $V_{1B}$ receptors are located in the anterior pituitary, and mediate adrenocorticotropic hormone (ACTH) release. $V_2$ receptors are located in the collecting ducts of the kidney; they are coupled to aquaporin channels and modulate free water clearance. Arginine vasopressin is released into the circulation in response to an increase in plasma osmolality (mediated by osmoreceptors) or a decrease in plasma volume or blood pressure (mediated by baroceptors). However, there are other stimuli for AVP release, including norepinephrine, angiotensin II, emotion, nausea and vomiting, and fever.

Heart failure is characterized by increased sympathetic nervous system activity and changes in several neurohormonal factors, such as angiotensin II, aldosterone, endothelin-1, and atrial natriuretic factor. In patients with advanced CHF, plasma levels of AVP are also increased. While the mechanism of AVP release in CHF is not well-understood, infusion of AVP into CHF patients results in an increase in systemic vascular resistance and a redistribution of cardiac output. These observations suggest that the increased levels of AVP observed in patients with severe CHF play a role in the pathogenesis of this disease. Several compounds are known which antagonize the hormonal effects of AVP, for example, the benzazepines disclosed in U.S. Pat. No. 5,723,606.

The cardiac dysfunction underlying CHF results in a decreased effective tissue perfusion, which in turn stimulates the renin-angiotensin-aldosterone and sympathetic nervous systems to promote $Na^+$ retention by the kidney, which can result in the formation of edema. Patients with CHF and evidence of pulmonary congestion or peripheral edema are routinely treated with diuretics. Thiazide diuretics, which act on the distal convoluted tubule of the kidney by inhibiting the $Na^+$—$Cl^-$ cotransporter, may initially be employed. However, they produce only a slight increase (5%–8%) in the amount of sodium excretion by the kidney, and subject the patient to risk of hypokalemia (low blood potassium) and hyponatremia. In patients with more advanced heart failure and signs of extracellular fluid accumulation, loop diuretics are generally used. Loop diuretics, such as furosemide, act at the thick ascending limb of the loop of Henle by competing for the $Cl^-$ site on the $Na^+$—$K^+$—$Cl^-$ transporter. These diuretics are capable of increasing the fractional sodium excretion to more than 20% of the filtered load, albeit at an even greater risk of potassium wasting in the urine and hypokalemia and hyponatremia in the serum.

We have now discovered that the use of diuretics in combination with compounds which inhibit vasopressin enzymes is surprisingly effective in promoting increased clearance of fluid by the kidney, and decreased excretion of sodium and potassium in the urine, thereby minimizing the risk of electrolyte disturbance such as hypokalemia and hyponatremia. An object of this invention is thus to provide compositions comprising a vasopressin antagonist in combination with a loop diuretic agent, and a method for treating edematous conditions such as CHF using such compositions.

SUMMARY OF THE INVENTION

This invention provides a composition comprising a diuretic agent and a vasopressin antagonist. The invention also provides a method for treating edematous conditions such as CHF, and promoting increased fluid clearance by the kidney, and maintenance of electrolyte balance in a mammal by decreasing excretion of sodium and potassium in the urine otherwise caused by the diuretic agent alone.

Any diuretic agent can be used in combination with any vasopressin antagonist according to this invention. In a preferred embodiment, the diuretic agent is a loop diuretic agent. Loop diuretics are compounds that act on the ascending limb of the loop of Henle and on the proximal and distal tubes in the kidneys of animals. The compounds are routinely used to treat edema associated with CHF, cirrhosis of the liver, and renal disease. Typical loop diuretics include bumetinide, ethacrynic acid, furosemide, piretanide, and torsemide. Other diuretics can also be used in this invention, including agents such as chlorothiazide, hydrochlorothiazide, triamterene, spironolactone, eplerenone, metolazone, acetazolamide, amiloride, and polythiozide. A preferred loop diuretic is furosemide (see U.S. Pat. No. 5,256,687).

The vasopressin antagonist to be employed is any chemical compound that is effective in inhibiting the biological activity of any arginine vasopressin or antidiuretic hormone. Numerous compounds are known to be vasopressin antagonists, and any of such compounds can be utilized in the composition of this invention.

In a preferred embodiment, the vasopressin antagonist to be utilized is a condensed benzazepine such as those described in U.S. Pat. No. 5,723,606, incorporated herein by reference. In a further preferred embodiment, the vasopressin antagonist is an imidazo benzazepine of the Formula I

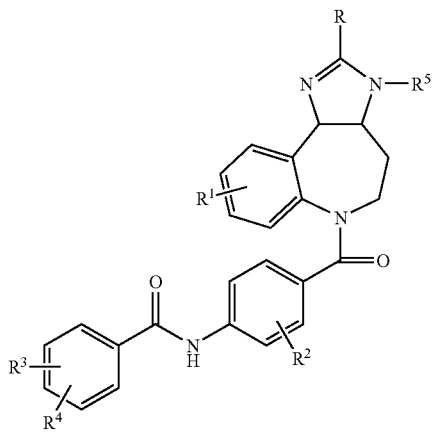

wherein R and $R^5$ are hydrogen or lower alkyl;
$R^1$, $R^2$, and $R^3$ independently are hydrogen, halo, lower alkyl, lower alkoxy, amino, alkylamino, or dialkylamino; and
$R^4$ is hydrogen, phenyl or substituted phenyl, and pharmaceutically acceptable salts thereof.

An especially preferred vasopressin antagonist to be used in accordance with this invention is conivaptan, which is N-[4-(2-methyl-4,5,6-tetrahydromidazo[4,5-d][1]benzazepin-6-ylcarbonyl)phenyl]biphenyl-2-carboxamide hydrochloride. Conivaptan is also referred to as CI-1025 and YM087, and has the structural formula below

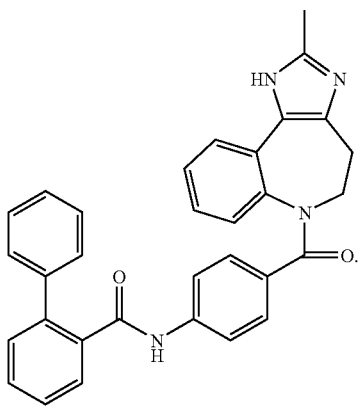

Other vasopressin antagonists that can be employed accordingly to this invention include the benzoheterocyclic compounds described in U.S. Pat. No. 5,258,510, incorporated herein by reference. Preferred compounds from this class to be used herein include the following:

5-Dimethylamino-1-[4-(2-methylbenzoylamino)-benzoyl]-2,3,4,5-tetrahydro-1H-benzazepine;

5-Dimethylamino-1-[2-chloro-4-(2-methylbenzoylamino)benzoyl]-2,3,4,5-tetrahydro-1H-benzazepine;

5-Methylamino-1-[2-chloro-4-(2-methylbenzoylamino)benzoyl]-2,3,4,5-tetrahydro-1H-benzazepine;

5-Cyclopropylamino-1-[2-chloro-4-(2-methylbenzoylamino)benzoxyl]-2,3,4,5-tetrahydro-1H-benzazepine;

5-Cyclopropylamino-1-[2-chloro-4-(2-chlorobenzoylamino)benzoxyl]-2,3,4,5-tetrahydro-1H-benzazepine;

5-Dimethylamino-1-[2-methyl-4-(2-methylbenzoylamino)benzoyl]-2,3,4,5-tetrahydro-1H-benzazepine;

5-Dimethylamino-1-[2-methoxy-4-(2-methylbenzoylamino)benzoyl]-1,2,3,4-tetrahydroquinoline;

7-Chloro-5-methylamino-1-[4-(2-methylbenzoylamino)benzoxyl]-2,3,4,5-tetrahydro-1H-benzazepine; and 7-Chloro-5-methylamino-1-[4-(2-chlorobenzoylamino)benzoxyl]-2,3,4,5-tetrahydro-1H-benzazepine.

Other vasopressin antagonists that can be employed according to this invention include those described in U.S. Pat. Nos. 5,225,402; 5,258,510; 5,338,755; 5,719,155; and 5,710,150, all of which are incorporated herein by reference. Specific vasopressin antagonists include YM471, OPC-31260, OPC-21268, OPC-41061, SR-121463, SR-49059, VPA-985, CL-385004, FR-161282, JVT-605, VP-339, WAY-140288, and the like.

The compositions provided by this invention will contain a diuretic agent, preferably a loop diuretic, and a vasopressin antagonist in a weight ratio of about 0.05:1 to about 1000:1, and typically about 1:1 to about 500:1 and ideally about 1:1 to about 10:1. A typical composition, for example, will comprise about 40 mg to about 80 mg of the loop diuretic furosemide together with about 5 mg to about 40 mg of conivaptan. Such compositions will be administered to adult humans suffering from edematous conditions such as CHF.

A further embodiment of this invention is a method for treating CHF comprising administering to a patient suffering from CHF and in need of treatment an effective amount of a diuretic agent in combination with an effective amount of vasopressin antagonist.

Another embodiment is a method for decreasing the excretion of sodium and potassium ions in the urine of an animal comprising administering a diuretic agent in combination with a vasopressin antagonist.

Still another embodiment of the invention is a method for increasing the amount of fluids secreted by an animal via the kidney comprising administering an effective amount of diuretic agent in combination with a vasopressin antagonist.

Another embodiment is a method for treating edematous states.

All that is required to practice the methods of this invention is to administer amounts of a diuretic agent and a vasopressin antagonist that are effective to treat CHF and to reduce electrolyte imbalance in mammals. The agents can be administered individually, or they can be formulated together into a single composition.

DETAILED DESCRIPTION OF THE INVENTION

Figure 1:
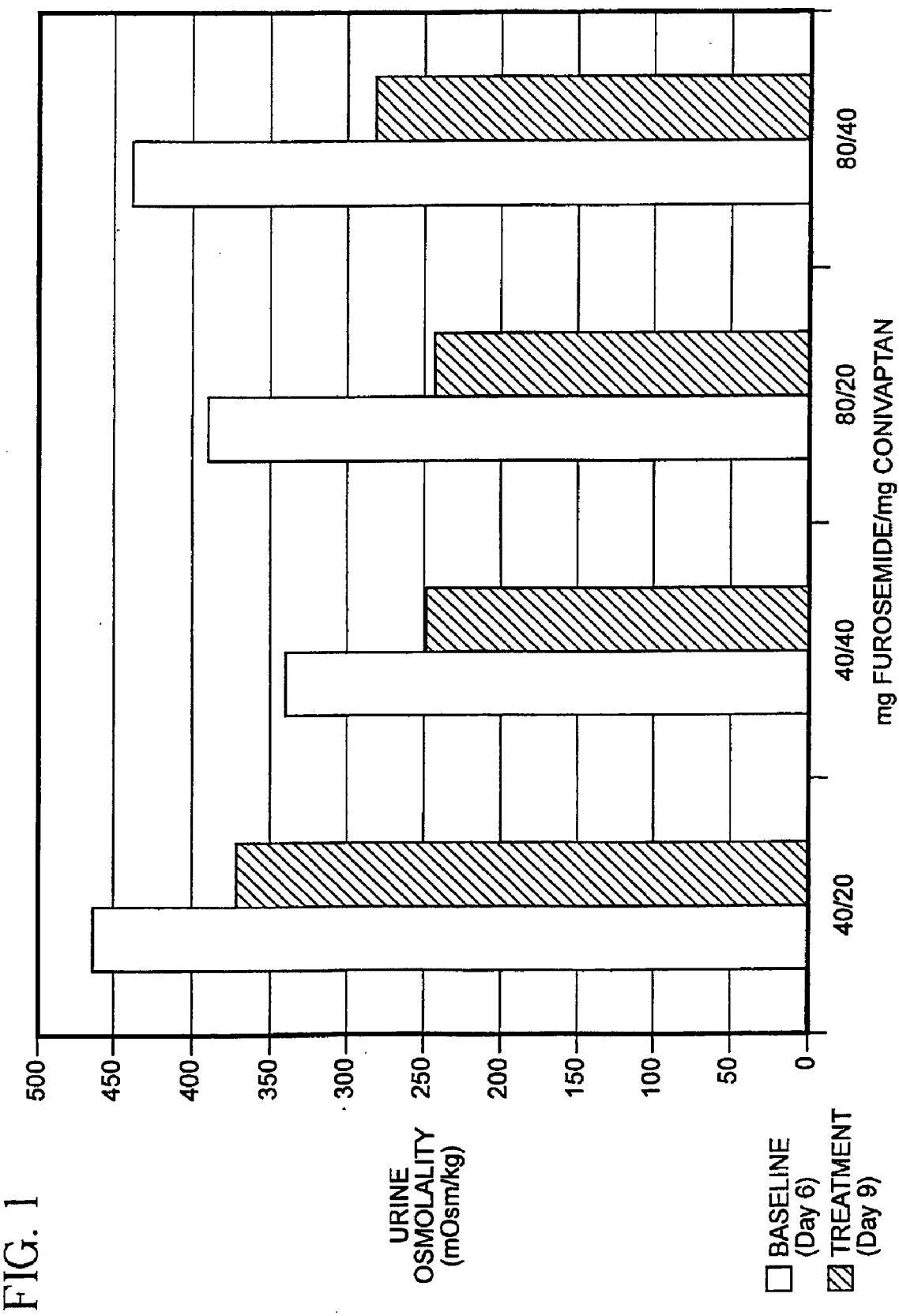
FIG. 1 shows the change in urine osmolality (mOsm/kg) in patients receiving various dose combinations of furosemide and conivaptan.

The ability of a combination of a diuretic agent together with a vasopressin antagonist to reduce electrolyte imbalance and to treat CHF has been established in a controlled clinical trial.

Preclinical pharmacologic studies have demonstrated potent binding of YM087 conivaptan to AVP receptors and antagonism of the vascular and renal effects of AVP. YM087 has high affinity for $V_{1A}$- and $V_2$-receptors with pKi (negative log of the binding inhibition constant) of 8.20 for human $V_{1A}$-receptors and 8.95 for human $V_2$-receptors expressed in COS-1 cells.

Clinical Pharmacology

YM087 given orally to rats antagonizes the AVP-induced pressor response ($V_{1A}$ antagonism) in a dose-related manner, with the dose that reduced the AVP response by 50% ($ID_{50}$) being 0.32 mg/kg; $ID_{50}$ for a similar experiment using intravenous (IV) YM087 in dogs was 0.026 mg/kg. In conscious dogs, oral YM087 (0.03 to 0.3 mg/kg) increased urinary output (V2 antagonism) and reduced urinary osmolality (from 1500 to <100 mOsm/kg $H_2O$) in a dose-related manner. Unlike furosemide, YM087 has little or no effect on urinary sodium (Na) or potassium (K) excretion. In dogs with heart failure induced by rapid right ventricular pacing, intravenous administration of YM087 (0.1 mg/kg) significantly improved the depressed cardiac function and produced a water diuresis.

Oral absorption of YM087 is rapid (peak concentrations reached between 0.5 to 1 hour in the rat and dog, respectively) and occurs predominantly in the small intestine. There is a marked food effect with absorption reduced by >50% in dogs after a meal. The elimination half-life is 1 hour in rats and 2 hours in dogs. Mass balance studies show the majority of radioactive tracer excreted in the feces. The preclinical toxicologic potential of YM087 has been extensively evaluated, and all findings were evaluated for relevance to human risk assessment and impact on clinical trial design. Findings of potential concern were bone marrow changes in dogs and effects on fertility in rats.

Histopathologic changes in bone marrow were observed in both 2- and 13-week oral studies in dogs with systemic exposures 28- to 87-fold higher than the maximum anticipated human exposure. Decreased peripheral erythrocyte, leukocyte, and/or platelet counts occurred in affected dogs in the 13-week study. Bone marrow and peripheral blood changes were reversible.

YM087 did not affect reproductive performance of male rats. In the 13-week, repeated oral dose study in rats, more females at 10 mg/kg were in diestrus or proestrus and fewer were in estrus than in controls, and uterine weights were decreased at all doses; associated systemic exposures were 0.06- to 3.2-fold the maximum anticipated human exposure. In the female fertility study in rats, reduced fertility index, increased implantation loss, and decreased live fetuses were observed in females given 100 mg/kg orally for 2 weeks prior to mating with untreated males. Effects on estrous cycle and fertility in female rats may be related to alterations in serum hormone levels resulting from pharmacologic activity of YM087. YM087 was not teratogenic in rats or rabbits.

Other drug-related effects, including diuresis and hepatocellular hypertrophy, were of less concern due to the nature of the effects or the high exposures at which the effects occurred compared to exposures anticipated in clinical trials.

YM087 was not mutagenic in bacteria, and was not clastogenic in human lymphocytes in vitro or in bone marrow of rats. No toxicity was observed in 4-week, IV studies with the glycerin formulation at maximum achievable doses, 2.5 mg/kg in rats and 2 mg/kg in dogs.

In summary, toxicological findings of potential concern for human risk assessment were reversible effects on bone marrow in dogs and reversible effects on estrus cycle and decreased fertility in rats. Findings in bone marrow were observed at exposures in excess of 23 times exposure expected in humans given the maximum dose of 120 mg once daily (QD), while effects on estrus cycle occurred at exposures from 0.05- to 3-fold the expected human exposure at 120 mg QD. Other drug-related findings in toxicology studies were considered secondary to pharmacologic activity or a functional adaptation to exposure to YM087.

YM087 has been given to approximately 250 healthy patients who participated in a total of 15 Phase 1 studies (8 in Japan and 7 in Europe). Subjects taking oral medication received either a single dose of YM087 (dose range 0.2 through 120 mg) QD or 30 or 120 mg YM087 administered as a divided dose twice daily (BID). Subjects received YM087 as a single IV injection once daily over a dose range of 0.2 to 250 µg/kg or up to a maximum of 50 mg.

Inhibition of AVP-induced platelet aggregation (evidence of $V_{1A}$ antagonist activity) was seen among subjects who received YM087 at 20 mg/day orally or 2.5 mg IV. Total inhibition of AVP-induced dermal vasoconstriction was observed among subjects who received YM087 50 mg IV.

Normal subjects have demonstrated aquaretic action (evidence of $V_2$-receptor antagonism) accompanied by a decrease in urine osmolarity starting at 15 mg oral or 50 µg/kg IV. At higher doses aquaretic effects were more pronounced and at 120 mg QD or 60 mg BID given orally or 50 mg given IV were considered too uncomfortable in normal subjects to be tolerable. YM087 at IV doses up to 250 µg/kg and 50 mg/day increased urine production rate for up to 3 and 6 hours postdosing, respectively.

Under fasting conditions, YM087 is rapidly absorbed, time to maximum plasma concentration (tmax) being reached at around 1 hour. The mean oral bioavailability of a 60-mg dose is 44% under fasting conditions; bioavailability is decreased after intake with food. A high-fat breakfast reduced bioavailability of single 15- to 90-mg doses of YM087 to 43% to 59% of the fasted value, and peak plasma levels were reduced to 24% to 54% of the fasting value. Oral YM087 demonstrated a nonlinear pharmacokinetic profile. Repeated BID oral doses of YM087, 60 mg, result in unexpectedly high plasma levels after the second dose, possibly caused by reduced first-pass metabolism. YM087 displays 2 compartment pharmacokinetics, with an elimination half-life of 4 to 5 hours. Elderly subjects have a similar elimination half-life as healthy, young volunteers.

The pharmacokinetics of orally administered YM087 (20 mg) were not affected when combined with either 0.5 mg IV digoxin or 25 mg oral captopril (each given as a single dose).

Safety

Among approximately 250 subjects treated, no major safety concerns were identified. One patient with severe CHF who received YM087 80 mg/day for 4 days experienced a generalized tonic clonic seizure, which the investigator could not exclude as related to study drug. The most frequent adverse events regardless of treatment association were mild or moderate thirst and mild headache. Other adverse events included flushes, a sensation of cold extremities, abdominal complaints, abnormal stools, syncope, dizziness, palpitations, and postural hypotension. Three subjects who received YM087 and one subject who received placebo developed minor, reversible decreases in white blood cell counts. No drug-related trend was observed in biochemical or hematological laboratory parameters. At higher doses, urinary osmolarity decreased and plasma osmolarity increased with or without an increase in plasma sodium. These observations were considered related to antagonism of $V_2$ receptors and not a safety concern. Vital signs (blood pressure and heart rate) were unaffected by YM087.

Study Rationale

The edematous condition resulting from CHF develops from a decreased effective tissue perfusion, which in turn stimulates the renin-angiotensin-aldosterone and sympathetic nervous systems to promote $Na^+$ retention by the kidney, which can result in the formation of edema. Patients with CHF and evidence of edema are routinely treated with diuretics. Thiazide diuretics, which act on the distal convoluted tubule of the kidney by inhibiting the $Na^+$—$Cl^-$ cotransporter, may initially be employed. However, they produce only a slight increase (5%–8%) in the amount of sodium excretion by the kidney and expose the patient to risk of hypokalemia and other disorders associated with electrolyte disorders. In patients with more advanced heart failure and signs of extracellular fluid accumulation, loop diuretics are generally used. Loop diuretics, such as furosemide, act at the thick ascending limb of the loop of Henle by competing for the $Cl^-$ site on the $Na^+$—$K^+$—$Cl^-$ transporter. These diuretics are capable of increasing the fractional sodium excretion to more than 20% of the filtered load, albeit at an even greater risk of hypokalemia and other electrolyte disorders.

At the kidney, AVP acts via the $V_2$ receptors in the principal cells of the collecting duct to increase water reabsorption. The binding of AVP to $V_2$ receptors results in an increase in cytosolic cAMP (via a linked G protein) which acts as a second messenger, and results in an increase in the "trafficking" of aquaporin 2 (AQP2) water channels from intracellular vesicles to the apical plasma membrane of the principal cells. While this shuttling of AQP2 occurs shortly following stimulation of the $V_2$ receptor, longer-term changes also occur in the form of an increase in AQP2 proteins. As YM087 antagonizes the binding of AVP to the $V_2$ receptor, it is reasonable to postulate that its mechanism of action is via the decrease in the trafficking and production of AQP2 to the plasma membrane of the principal cells of the collecting duct.

These findings indicate that furosemide and YM087 act at different segments of the nephron, and act via different mechanisms of action. Agents that act at different portions of the kidney can be of importance in patients with CHF and other edematous states who sometimes develop resistance to loop diuretics, especially when they have been used chronically for some time. The addition of a hormone antagonist which would increase the excretion of solute-free water (and thus not increase sodium loss) and simultaneously limit potassium losses, might produce an added benefit in the treatment of CHF patients who are currently on a loop diuretic. Therefore, this study will be conducted to assess the effect of concomitant treatment with the vasopressin antagonist, YM087, and a commonly used diuretic, furosemide, in patients with a prototypical edematous condition, namely CHF.

Study Objectives

The objectives of this study are:

To assess the effect of concomitant treatment with YM087 and furosemide in CHF patients;

To determine the safety of giving these two agents concomitantly to CHF patients; and To assess the pharmacodynamic parameters of oral YM087 when given with furosemide Study Design This is an open-label, randomized study assessing the effect on the safety and efficacy of oral YM087 (20 or 40 mg QD) when given concomitantly with oral furosemide (40 or 80 mg QD) to patients with CHF.

This study is comprised of 4 phases: Screening, Furosemide Balance, Baseline, and Treatment (Scheme 1, Study Design). Patients will be randomized to 1 of 4 treatment combinations: (a) furosemide 40 mg QD and YM087 20 mg QD; (b) furosemide 40 mg QD and YM087 40 mg QD; (c) furosemide 80 mg QD and YM087 20 mg QD; or (d) furosemide 80 mg QD and YM087 40 mg QD. Patients will be treated on an outpatient basis, and will come for clinic visits at Screening and on Study Days 1, end of Day 4 (beginning of Day 5), and each day of treatment (Days 5 through 9 [beginning of Day 10]). All tests scheduled to be done at the 24-hour time point will be done prior to the next dose of study medication. Urine collections will be done for the 24 hours prior to the visit.

Scheme 1. Study Design Schematic

| | | | | |
|---|---|---|---|---|
| YM087 | | | | 20 mg QD |
| Furosemide | 40 mg QD | 40 mg QD | 40 mg QD | |
| | | | | |
| YM087 | | | | 40 mg QD |
| Furosemide | 40 mg QD | 40 mg QD | 40 mg QD | |
| | | | | |
| YM087 | | | | 20 mg QD |
| Furosemide | 80 mg QD | 80 mg QD | 80 mg QD | |
| | | | | |
| YM087 | | | | 40 mg QD |
| Furosemide | 80 mg QD | 80 mg QD | 80 mg QD | |
| Phase | Screening | Furosemide Balance | Baseline | Treatment |
| Length of Phase (days) | 1 | 4 | 2 | 3 |
| Study Day | Between -7 to -1 | 1–4 | 5–6 | 7–9 |

Study Schedule

Screening Phase (1 Week)

The Screening Phase allows the investigator to evaluate patients who qualify for entry into the study and to assess initial values for a number of study parameters (ie, clinical laboratory and urinalysis values including serum and urine electrolytes). An informed consent will be signed and patients will provide medical history, including documentation of New York Heart Association (NYHA) Class II/III CHF. A physical examination will also be performed at this time.

Furosemide Balance Phase (4 Days)

This phase allows the patient to achieve sodium and fluid balance on the background dose of furosemide. The patient will be randomized to 1 of the 4 arms of the study, and during this phase, will receive the dose of furosemide (either 40 or 80 mg/day) to which he/she is randomized. The dose should be given in the morning (before breakfast). During this phase and throughout the remainder of the study, patients will monitor their weight daily.

Baseline Phase (2 Days)

During the Baseline Phase, the patient will continue to receive the dose of furosemide (either 40 or 80 mg/day) to which he/she has been randomized. Patients will be given their dose of furosemide in the clinic for each of these days. This phase will be used to establish baseline values for a number of study parameters. Various clinical laboratory parameters (eg, serum and urine sodium, and plasma and urine osmolalities), free water clearance, effective water clearance, and safety profiles will be obtained. On Day 6, patients will remain in the clinic during the first 6 hours of the study in order to collect blood and urine samples at various time points. Patients will then be allowed to return home overnight (continuing to collect their urine for the 24-hour urine sample), and will return to the clinic the following morning at their scheduled visit.

Treatment Phase (3 Days)

This phase is used to determine the effect of concomitant treatment with furosemide and YM087. In addition to the background dose of furosemide (40 or 80 mg/day), patients will receive YM087 at the dose to which they have been randomized (20 or 40 mg QD) for 3 days (Study Days 7–9). Both drugs will be administered at the same time orally once daily 1 hour before breakfast with 100 mL water. Furosemide and YM087 will be dispensed in the clinic on these days (Study Days 7, 8, and 9). On Day 9, patients will remain in the clinic during the first 6 hours of the study, in order to collect blood and urine samples at various time points. Patients will then be allowed to return home overnight (continuing to collect their urine for the 24-hour urine sample), and will return to the clinic the following morning for their scheduled visit.

If at any time, the investigator judges the patient's volume status to be abnormally decreased, the next dose of furosemide may be decreased by one-half. The dose of furosemide can be further decreased by one-half at any later assessment in which the volume status is still abnormal.

Fluid and Sodium Intake

Patients will have their sodium and fluid intake assessed prior to the Baseline Phase. CBF patients should be maintained on the sodium-restricted diet that is typically prescribed for these patients. A dietician or nurse coordinator will determine the contents of diet and daily calorie intake, salt consumption, and volume of water consumed in the diet. These levels will be maintained throughout the study period. Total fluid intake (not including water in food) may not exceed 2.0 L/day. Fluid intake will be assessed on a daily basis.

Urine Output

A 24-hour urine specimen will be collected on Study Days 4 through 9. Samples will be collected at intervals on Study Days 6 and 9, and subsequently pooled to obtain the total 24-hour sample. Urine collection will begin following the administration of furosemide alone or furosemide and YM087 (at approximately 7 AM).

Study Population

Source and Number of Patients

Number of Patients: 3 to 6 patients per arm; 12 to 24 patients total Source: Outpatients Patient-Selection Criteria Inclusion Criteria These criteria are mandatory and must be met to provide evaluable data.

Males or females 18 to 85 years of age
  Females must be postmenopausal, surgically sterilized or practicing a barrier method of birth control so that in the opinion of the investigator, they will not become pregnant during the study;
Congestive heart failure with Class II or III functional impairment by New York Heart Association criteria (Appendix C);
  At screening, current therapy for chronic heart failure consisting of at least 2 months duration of an ACE inhibitor, β-blocker (optional), and digoxin (optional);
  Doses of digoxin, ACE inhibitors, and/or β-blockers, must have been held constant for 7 days prior to the Balance Phase; and
  At screening, patients must have been receiving a dose of furosemide of between 40 and 160 mg/day.

Exclusion Criteria

Breast-feeding or pregnant;
Excessive peripheral edema (>2+, ie, above the knee) or lack of peripheral edema, suggesting volume depletion;
Significant renal impairment (serum creatinine >2.5 mg/dL or creatinine clearance <30 mL/min); or nephrotic syndrome;
Known urinary outflow obstruction (eg, stenosis, stone, tumor, etc);
Alanine aminotransferase (ALT) or aspartate aminotransferase (AST) >3×upper limit of normal (ULN) and/or bilirubin $\geq$2.5 mg/dL; or cirrhosis with ascites;
Active myocarditis, constrictive pericarditis, or active vasculitis due to collagen vascular disease;
Uncontrolled hyper- or hypothyroidism;
Adrenal insufficiency (AM cortisol <7 µg/dL);
Serious hematological diseases (eg, severe anemia, Hgb <10 g/dL; leukopenia, WBC <4000/µL);
Significant hypotension (SBP <95) or uncontrolled hypertension;
Concurrent enrollment in a chemotherapy or radiation regimen;
Unstable angina or acute myocardial infarction within 30 days of the screening visit;
Treatment with inotropic drugs (eg, dobutamine, dopamine, milrinone, amrinone, etc) within 30 days of the screening visit;
Participation in another clinical trial of an investigational drug (including placebo) within the 30 days prior to screening for entry into the present study;
History of current or past use of illicit drugs or alcoholism unless abstinence can be documented for $\geq$6 months;
Other medical conditions, such as significant obstructive cardiac valvular disease and/or hypertrophic subaortic stenosis, obstructive lung disease, dementia, or significant abnormalities that the investigator feels may compromise the patient's safety or successful participation in the study; and Inability to understand and sign the Informed Consent to participate in this study.

Prohibited Drugs

The following medications may not be taken during this study:

Any antineoplastic agent;

Any medication known to cause leukopenia;

Parenteral inotropic agents;

Nonsteroidal anti-inflammatory drugs, with the exception of low-dose aspirin ($\leq 325$ mg/day); and Smoking pattern should not be altered for the duration of the investigation, as smoking has been found to stimulate the secretion of AVP from the posterior pituitary gland. Patients must not smoke immediately prior to blood sampling.

Allowable Medications

Digitalis, ACE inhibitors, beta blockers, or other vasodilators are allowed but should be at a stable dose for at least 7 days prior to the Furosemide Balance Phase. The dosage and regimen of any other chronic, permitted concurrent medications (eg, hormone replacement therapy, hormone contraceptives, thyroid replacement therapy, or H2 antagonists) should be stabilized before the Furosemide Balance Phase and held constant throughout the study. Any medications prescribed chronically or intermittently during the study or dose adjustments of these medications must be reported on the concurrent medication Case Report Form (CRF). It is recommended that concurrent medications not be taken at the same time as the study drug (eg, within 1–2 hours).

Efficacy Assessments

Primary Efficacy Parameter(s)

The primary efficacy measure is change in urine output from baseline (obtained on Day 2 of the Baseline Phase [Study Day 6]) to end of treatment (Study Day 9).

Secondary Efficacy Parameter(s)

Similarly, secondary efficacy parameters will be evaluated:

Change from baseline in body weight; and

Change from baseline in free water clearance, calculated as $$C_{H_2O} = V\left(1 - \frac{Uosm}{Posm}\right)$$

where: V=Urine volume (mL/day);

Uosm=Urine osmolality, and

Posm=Plasma osmolality.

Change from baseline in effective water clearance, calculated as $$V - [2(U_{Na} + U_K) \times V/2(P_{Na} + P_K)]$$

where: V=Urine volume;

$U_{Na}$=Urine sodium concentration;

$U_K$=Urine potassium concentration;

$P_{Na}$=Plasma sodium concentration; and $P_K$=Plasma potassium concentration.

This formula can be reduced to:

$$V \times \left(1 - \frac{U_{Na} + U_K}{P_{Na} + P_K}\right)$$

Change from baseline in serum and urine sodium;

Change from baseline in fractional sodium excretion, calculated as:

$$Fe_{Na}\% = \frac{CL_{Na}}{CL_{CR}} \times 100$$

where: $CL_{Na}$=sodium clearance; and $CL_{CR}$=creatinine clearance.

Number of back-titrations of furosemide

Laboratory Evaluation

Full clinical laboratory assessments will be performed at screening and at the end of Study Days 6 and 9. A clinically significant laboratory abnormality occurring during the study that has been verified by repeat testing will be reported as an adverse event and followed until the abnormality has resolved or a satisfactory explanation has been obtained (see Appendix B for a listing of the clinical laboratory determinations to be performed).

Urinalysis

A urinalysis will be performed at screening and at the end of the study (Day 9).

Other Assessments

Pharmacokinetic/Pharmacodynamic Analysis

Plasma concentrations of YM087 and plasma and urine concentrations of furosemide will be determined throughout the study as outlined in Appendix A. YM087 concentrations will be measured using a validated LC/MS/MS method in the positive ionization mode. Furosemide concentrations will be determined using a validated HPLC method. For both assays, sensitivity, specificity, linearity, and reproducibility will be determined before analysis of samples.

A pharmacokinetic/pharmacodynamic analysis will be utilized to evaluate the potential effect of concomitant treatment with YM087 and furosemide in comparison to furosemide alone. In addition, plasma concentrations of furosemide during baseline and treatment phases, will give information about a potential pharmacokinetic interaction between YM087 and furosemide.

Study Medication

Description

Furosemide tablets (40 and 80 mg) and YM087 tablets (10 mg) will be prepared for the study by the Clinical Pharmaceutical Operations Department. Medication for this protocol will be dispensed according to the randomization code. All study medications should be stored in a secure, locked area. A detailed set of dispensing instructions will be included with the drug shipment.

Data Analysis and Statistical Considerations

Power and Sample Size

This is an exploratory study. Patient numbers are not based on considerations of power, but are thought to be adequate to provide preliminary assessment of the safety and tolerability of YM087 when administered concomitantly with furosemide.

Efficacy Parameters

The efficacy parameters and changes from baseline will be summarized by treatment group at each collection time. Baseline values are defined as those values obtained at the 24 hour time point of Study Day 6 (end of Baseline Phase). Descriptive statistics will include mean, standard error, median, minimum, maximum, and others as appropriate.

A urine creatinine will be obtained on all 24-hour urine specimens in order to determine the accuracy of urine collection. Results will be summarized on those urine samples determined to be complete 24-hour collections. Additionally, results from all patients will be summarized.

Twenty-four patients ranging in age from 41 to 87 with Class II/Class III CHF (as defined by the New York Heart Association) were randomized into 1 of 4 treatment groups. Group I received 40 mg of furosemide alone, once a day for 6 days, followed by concomitant treatment with 20 mg of conivaptan once a day for 3 days. Group II received initial dosing with 40 mg of furosemide, followed by concomitant dosing with 40 mg of conivaptan. Group III received 80 mg of furosemide initially, then concomitant dosing with 20 mg of conivaptan. Group IV received 80 mg of furosemide alone, and then in continuation with 40 mg of conivaptan.

Figure 2:
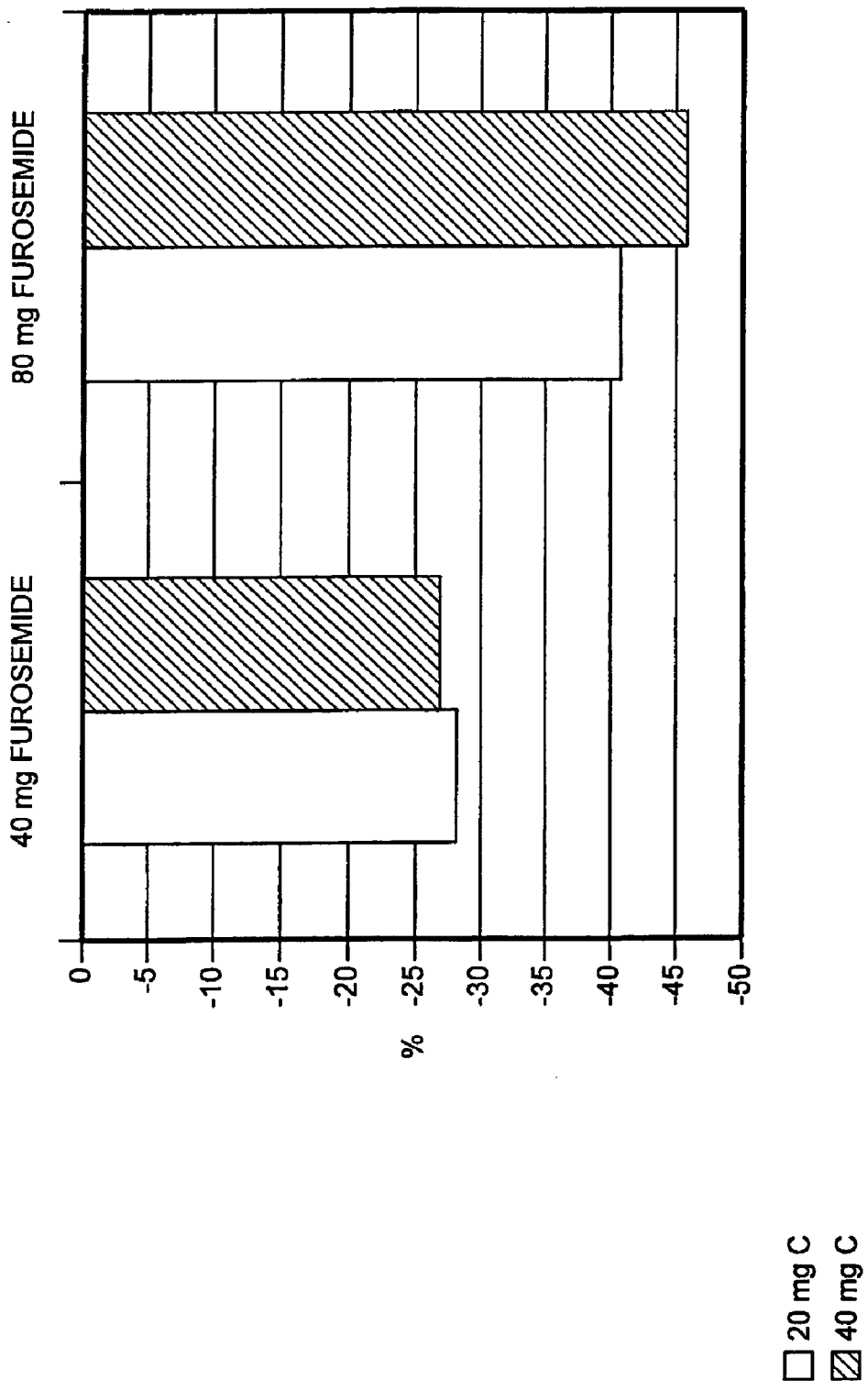
FIG. 2 shows the percentage reduction in urine osmolality caused by various dose combinations of furosemide and conivaptan and the synergy between the two agents.
Figure 3:
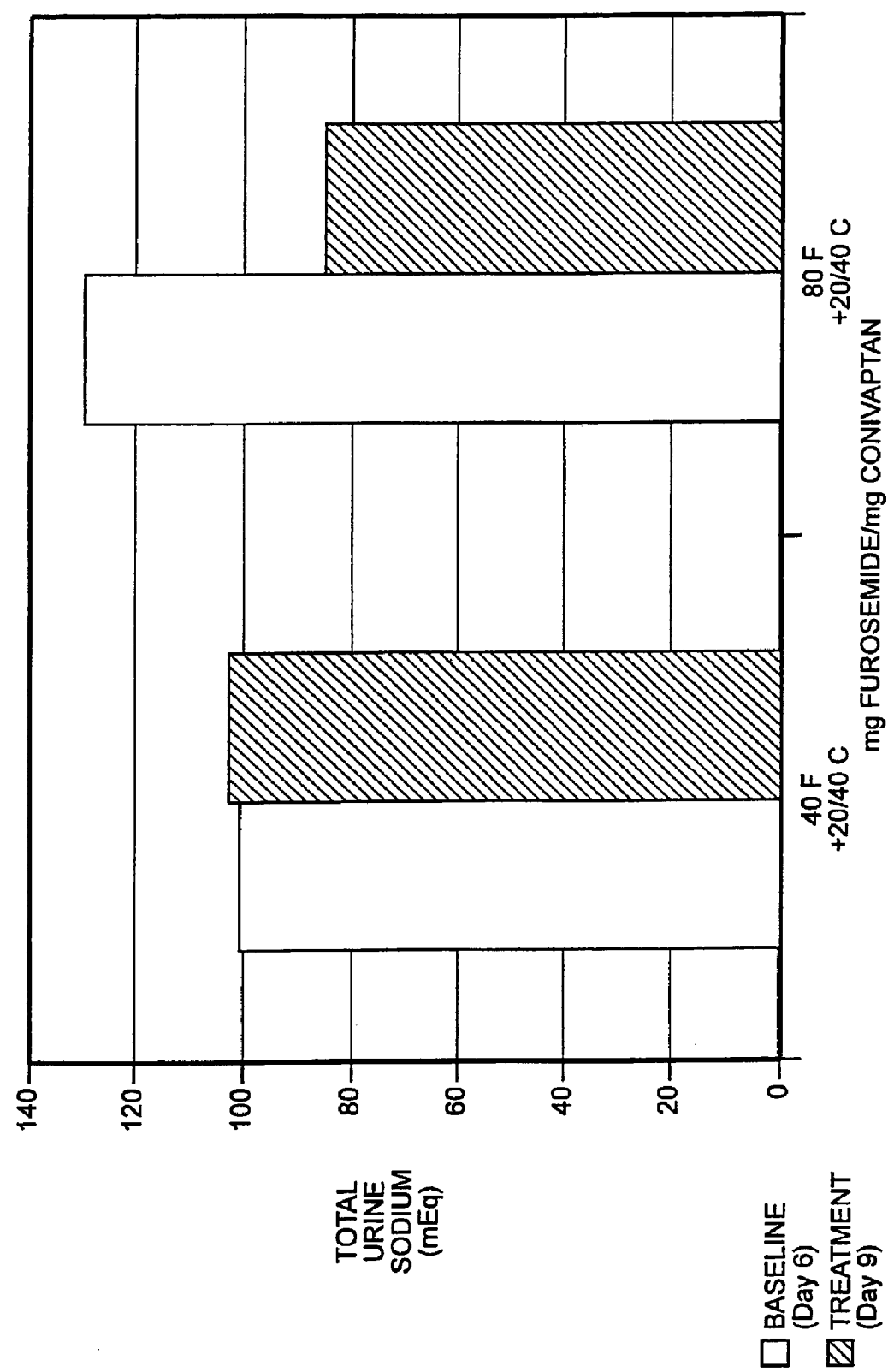
FIG. 3 shows the total urine sodium concentration (mEq) following various dose combinations of furosemide and conivaptan (conivaptan antagonizes the excretion of sodium).
Figure 4:
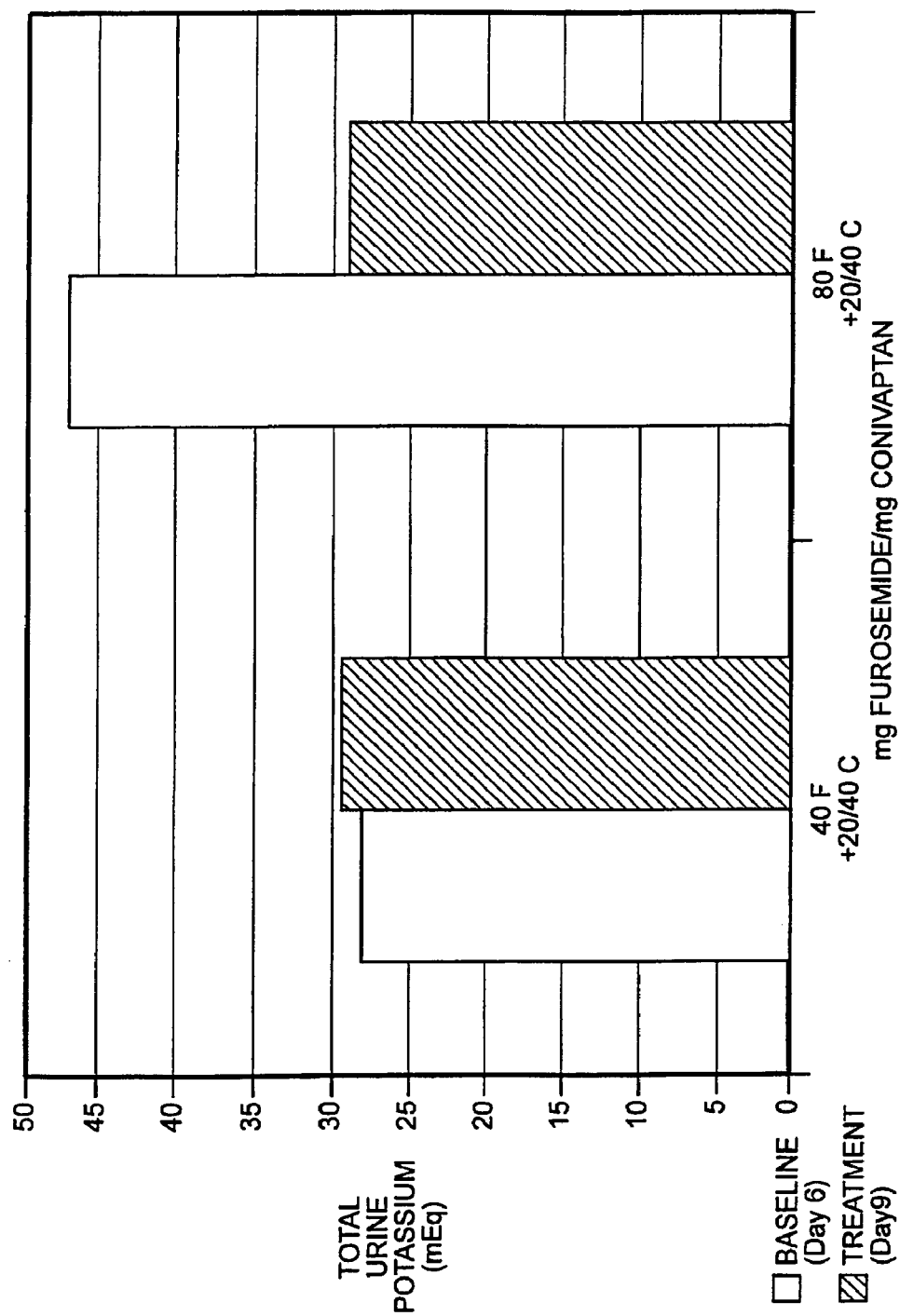
FIG. 4 shows the total urine potassium concentration (mEq) following various dose combinations of furosemide and conivaptan. Conivaptan antagonizes the urinary excretion of potassium by furosemide.

Baseline measurements of urine volume, osmolality, sodium, and potassium content were obtained on Day 6 (steady state for background furosemide use), and evaluations of the combination therapy were done on Day 9. The data shown in FIGS. 1 and 2 and in Table 1 below establish that the aquaretic effects of conivaptan not only persist but are amplified with concurrent use of a loop diuretic. This surprising result establishes synergism between the two drugs on urinary water excretion. In addition, the results of urinary sodium excretion shown in FIG. 3 and in Table 1 below establish that combination therapy lessens the loss of sodium in the urine, particularly as the dose of furosemide is increased. This surprising result renders the claimed combination particularly useful in treatment or prevention of hyponatremia in edematous states like CHF in which therapy with a diuretic is standard care. Finally, the results on urinary potassium excretion shown in FIG. 4 establishes that the combination substantially reduces potassium loss, particularly as the dose of furosemide is increased. This surprising result indicates the claimed combination is especially useful in treatment or prevention of hypokalemia in edematous states like CHF in which therapy with a diuretic is standard care. In total, the data establish that conivaptan in combination with a loop diuretic such as furosemide can provide increased therapeutic excretion of water in edematous conditions like CHF. Furthermore, the data establish that the deleterious effects of a loop diuretic on electrolyte loss, particularly potassium, can be diminished to a surprising extent by concomitant treatment with a vasopressin antagonist such as conivaptan.

TABLE 1

Change From Baseline in Pharmacodynamic Parameters (0–6 Hours Postdose)

| Treatment Group | Urine Osmolality (mOsm/kg) Mean % Change | Total Urine Sodium (mEq) Mean % Change | Total Urine Potassium (mEq) Mean % Change | Urine Volume (mL) Mean % Change |
|---|---|---|---|---|
| F 40 mg/C 20 mg | −25.0 | −13.8 | −1.3 | 54.4 |
| F 40 mg/C 40 mg | −13.4 | 27.6 | 14.0 | 79.9 |
| F 80 mg/C 20 mg | −43.2 | −9.2 | −23.1 | 13.7 |
| F 80 mg/C 40 mg | −45.5 | −32.3 | −45.0 | −7.8 |

F = Furosemide;
C = Conivaptan.

The compositions to be employed in the present invention can be prepared and administered in a wide variety of oral and parenteral dosage forms for treating and preventing edematous conditions such as CHF, and promoting electrolyte balance. The compounds can be administered by injection, that is, intravenously, intramuscularly, intracutaneously, subcutaneously, submucosally, intraductally, intraduodenally, or intraperitoneally. Also, the compounds can be administered by inhalation, for example, intranasally. Additionally, the compositions can be administered transdermally. It will be obvious to those skilled in the art that the following dosage forms may comprise as the active component, either a compound as a free base, acid, or a corresponding pharmaceutically acceptable salt of such compound. The active compound generally is present in a concentration of about 5% to about 95% by weight of the formulation.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from 5% or 10% to about 70% of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without other carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogenous mixture is then poured into convenient sized molds, allowed to cool, and thereby to solidify.

Liquid form preparations include solutions, suspensions, and emulsions, for example, water or water propylene glycol solutions. For parenteral injection, liquid preparations can be formulated in solution in aqueous polyethylene glycol solution.

Aqueous solutions suitable for oral use can be prepared by dissolving the active component in water and adding suitable colorants, flavors, stabilizing, and thickening agents as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of each active component in a unit-dose preparation may be varied or adjusted from 1 to 1000 mg, preferably 10 to 100 mg according to the particular application and the potency of the active component. The composition can, if desired, also contain other compatible therapeutic agents.

The following examples illustrate typical formulations that can be utilized in the invention.

| Tablet Formulation | |
|---|---|
| Ingredient | Amount (mg) |
| Conivaptan | 25 |
| Furosemide | 40 |
| Lactose | 30 |
| Cornstarch (for mix) | 10 |
| Cornstarch (paste) | 10 |
| Magnesium stearate (1%) | 5 |
| Total | 120 |

The conivaptan, furosemide, lactose, and cornstarch (for mix) are blended to uniformity. The cornstarch (for paste) is suspended in 200 mL of water and heated with stirring to form a paste. The paste is used to granulate the mixed powders. The wet granules are passed through a No. 8 hand screen and dried at 80° C. The dry granules are lubricated with the 1% magnesium stearate and pressed into a tablet. Such tablets can be administered to a human from one to four times a day for treatment of CHF and other edematous conditions.

| Preparation for Oral Solution | |
|---|---|
| Ingredient | Amount |
| Conivaptan | 40 mg |
| Furosemide | 80 mg |
| Sorbitol solution (70% N.F.) | 40 mL |
| Sodium benzoate | 20 mg |
| Saccharin | 5 mg |
| Red dye | 10 mg |
| Cherry flavor | 20 mg |
| Distilled water q.s. | 100 mL |

The sorbitol solution is added to 40 mL of distilled water, and the conivaptan and furosemide are dissolved therein. The saccharin, sodium benzoate, flavor, and dye are added and dissolved. The volume is adjusted to 100 mL with distilled water. Each milliliter of syrup contains 4 mg of invention composition. The composition is administered to animals to treat edematous states such as heart failure, hepatic failure, and venous insufficiency.

PARENTERAL SOLUTION

In a solution of 700 mL of propylene glycol and 200 mL of water for injection is suspended 20 g of conivaptan and 15 g of furosemide. After suspension is complete, the pH is adjusted to 6.5 with 1 N sodium hydroxide, and the volume is made up to 1000 mL with water for injection. The formulation is sterilized, filled into 5.0 mL ampoules each containing 2.0 ML, and sealed under nitrogen. The composition is administered to a patient in order to decrease the excretion of sodium and potassium in the urine, thereby preventing electrolyte imbalance associated with CKF and use of a diuretic agent alone.

What is claimed is:

1. A pharmaceutical composition comprising conivaptan and furosemide.

2. A method for treating congestive heart failure or other edematous conditions comprising administering to a mammal in need thereof an effective amount of a pharmaceutical composition of claim 1.

3. A method for inhibiting excretion of sodium ions in the urine of an animal comprising administering to the animal an effective amount of a pharmaceutical composition of claim 1.

4. A method for inhibiting excretion of potassium ions in the urine of an animal comprising administering to the animal an effective amount of a pharmaceutical composition of claim 1.

* * * * *